United States Patent
Plumptre (10) Patent No.: US 11,213,628 B2
(45) Date of Patent: Jan. 4, 2022

(54) BEARING COMPONENT FOR A PISTON ROD OF A DRUG DELIVERY DEVICE, PISTON ROD COMPRISING THE BEARING COMPONENT, AND DRUG DELIVERY DEVICE

(71) Applicant: Sanofi-Aventis Deutschland GmbH, Frankfurt am Main (DE)

(72) Inventor: David Aubrey Plumptre, Worcestershire (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 495 days.

(21) Appl. No.: 14/771,544

(22) PCT Filed: Mar. 10, 2014

(86) PCT No.: PCT/EP2014/054525
§ 371 (c)(1),
(2) Date: Aug. 31, 2015

(87) PCT Pub. No.: WO2014/139913
PCT Pub. Date: Sep. 18, 2014

(65) Prior Publication Data
US 2016/0015901 A1    Jan. 21, 2016

(30) Foreign Application Priority Data
Mar. 11, 2013   (EP) .................................... 13158513

(51) Int. Cl.
*A61M 5/315* (2006.01)

(52) U.S. Cl.
CPC .... *A61M 5/31515* (2013.01); *A61M 5/31551* (2013.01); *A61M 5/315* (2013.01);
(Continued)

(58) Field of Classification Search
CPC .......... A61M 5/31515; A61M 5/31501; A61M 5/31583; A61M 5/31511;
(Continued)

(56) References Cited

U.S. PATENT DOCUMENTS

| 533,575 A | 2/1895 | Wilkens |
| 2,895,773 A * | 7/1959 | McConnaughey .......................... A61M 5/31513 92/245 |

(Continued)

FOREIGN PATENT DOCUMENTS

| CA | 2138528 | 12/1998 |
| CA | 2359375 A1 | 7/2000 |

(Continued)

OTHER PUBLICATIONS

Extended European Search Report issued in European Patent Application No. 13158513.5, dated Jul. 23, 2013.

(Continued)

*Primary Examiner* — Emily L Schmidt
*Assistant Examiner* — Leah J Swanson
(74) *Attorney, Agent, or Firm* — Fish & Richardson P.C.

(57) ABSTRACT

The bearing component comprises a contact surface inside a periphery, which surrounds a centre, and a coupling feature arranged inside the periphery for rotatably engaging a component of a piston rod perpendicular to the contact surface. The coupling feature includes at least one flexible feature extending from the periphery towards the centre, and the flexible feature is arranged to be deflected towards the periphery by a force exerted on the flexible feature in a direction towards the contact surface and deflected towards the centre by a force exerted on the flexible feature in the opposite direction. The flexible feature may have a sloping surface facilitating assembly and preventing disassembly in (Continued)

combination with a further component of the piston rod. The component of the piston rod may be a lead screw, and the piston rod may be used in a drug delivery device.

21 Claims, 2 Drawing Sheets (52) U.S. Cl.
CPC ............... *A61M 5/31583* (2013.01); *A61M 2005/31508* (2013.01)

(58) Field of Classification Search
CPC ...... A61M 5/2422–5/2429; A61M 2005/2444; A61M 2005/2488; A61M 5/281; A61M 2005/31516; A61M 2005/31523; A61M 5/315; A61M 2005/31513
See application file for complete search history.

(56) References Cited

U.S. PATENT DOCUMENTS

| | | | |
|---|---|---|---|
| 4,865,591 A | 9/1989 | Sams | |
| 5,092,842 A | 3/1992 | Bechtold et al. | |
| 5,226,895 A | 7/1993 | Harris | |
| 5,226,896 A | 7/1993 | Harris | |
| 5,279,586 A | 1/1994 | Balkwill | |
| 5,304,152 A | 4/1994 | Sams | |
| 5,320,609 A | 6/1994 | Haber et al. | |
| 5,378,233 A | 1/1995 | Haber et al. | |
| 5,383,865 A | 1/1995 | Michel | |
| 5,391,157 A | 2/1995 | Harris et al. | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A * | 5/1997 | Petersen | A61M 5/31551 |
| | | | 222/309 |
| 5,674,204 A | 10/1997 | Chanoch | |
| 5,688,251 A | 11/1997 | Chanoch | |
| 5,688,252 A * | 11/1997 | Matsuda | A61M 5/2448 |
| | | | 604/218 |
| 5,735,825 A * | 4/1998 | Stevens | A61M 5/31513 |
| | | | 604/218 |
| 5,807,346 A | 9/1998 | Frezza | |
| 5,820,602 A | 10/1998 | Kovelman et al. | |
| 5,851,079 A | 12/1998 | Horstman et al. | |
| 5,921,966 A | 7/1999 | Bendek et al. | |
| 5,957,896 A | 9/1999 | Bendek et al. | |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,562,006 B1 | 5/2003 | Hjertman et al. | |
| 6,613,023 B2 | 9/2003 | Kirchhofer et al. | |
| 6,699,224 B2 | 3/2004 | Kirchhofer et al. | |
| 6,899,698 B2 | 5/2005 | Sams | |
| 6,932,794 B2 | 8/2005 | Giambattista et al. | |
| 6,936,032 B1 | 8/2005 | Bush, Jr. et al. | |
| 7,169,132 B2 | 1/2007 | Bendek et al. | |
| 7,241,278 B2 | 7/2007 | Moller | |
| 7,678,084 B2 | 3/2010 | Judson et al. | |
| 7,850,662 B2 | 12/2010 | Veasey et al. | |
| 8,186,233 B2 | 5/2012 | Joung et al. | |
| 2002/0052578 A1 | 5/2002 | Moller | |
| 2002/0120235 A1 | 8/2002 | Enggaard | |
| 2003/0050609 A1 | 3/2003 | Sams | |
| 2004/0059299 A1 | 3/2004 | Moller | |
| 2004/0097883 A1 | 5/2004 | Roe | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2006/0153693 A1 | 7/2006 | Fiechter et al. | |
| 2007/0016143 A1 | 1/2007 | Miller et al. | |
| 2007/0093761 A1 | 4/2007 | Veasey et al. | |
| 2009/0275916 A1 | 11/2009 | Harms et al. | |
| 2011/0319835 A1 | 12/2011 | Burren et al. | |
| 2012/0136298 A1 * | 5/2012 | Bendix | A61M 5/2448 |
| | | | 604/89 |
| 2012/0265151 A1 | 10/2012 | Nzike et al. | |
| 2013/0012888 A1 * | 1/2013 | Okihara | A61M 5/31515 |
| | | | 604/220 |
| 2013/0023831 A1 | 1/2013 | Helmer et al. | |
| 2015/0151043 A1 | 6/2015 | Graf et al. | |

FOREIGN PATENT DOCUMENTS

| | | | |
|---|---|---|---|
| CN | 1547492 | 11/2004 | |
| CN | 1780652 | 5/2006 | |
| CN | 102448520 | 5/2012 | |
| CN | 102573961 | 7/2012 | |
| CN | 102821803 | 12/2012 | |
| EP | 0496141 A1 | 7/1992 | |
| EP | 0897729 A2 | 2/1999 | |
| EP | 0937471 A2 | 8/1999 | |
| EP | 0937476 A2 | 8/1999 | |
| EP | 1776975 A2 | 4/2007 | |
| EP | 2438949 | 4/2012 | |
| EP | 2554204 A1 | 2/2013 | |
| JP | 2008-538719 | 11/2008 | |
| JP | 2012-045173 | 3/2012 | |
| JP | 2012532720 | 12/2012 | |
| RU | 2132703 | 7/1999 | |
| WO | 9307922 A1 | 4/1993 | |
| WO | 9324160 A1 | 12/1993 | |
| WO | WO 1994/025090 | 11/1994 | |
| WO | 9938554 A1 | 8/1999 | |
| WO | 0110484 A1 | 2/2001 | |
| WO | 0230495 A2 | 4/2002 | |
| WO | 02092153 A2 | 11/2002 | |
| WO | 03080160 A1 | 10/2003 | |
| WO | 2006084876 A1 | 8/2006 | |
| WO | WO 2006/114396 | 11/2006 | |
| WO | WO 2009/039851 | 4/2009 | |
| WO | WO 2010/110712 | 9/2010 | |
| WO | WO 2011/006924 | 1/2011 | |
| WO | 2011042539 A1 | 4/2011 | |
| WO | WO-2011039229 A1 * | 4/2011 | ........ A61M 5/31551 |
| WO | WO 2011/121867 | 10/2011 | |

OTHER PUBLICATIONS

Examination Report issued in Australian Patent Application No. 2014230959 dated Jul. 29, 2017.
"Pen-injectors for medical use—Part 1: Pen-injectors—Requirements and test methods," International Standard, reference No. ISO 11608-1:2000(E), first edition Dec. 15, 2000, 32 pages.
International Preliminary Report on Patentability in International Application No. PCT/EP2014/054525, dated Sep. 15, 2015, 7 pages.
International Search Report and Written Opinion in International Application No. PCT/EP2014/054525, dated May 20, 2014, 11 pages.

* cited by examiner

BEARING COMPONENT FOR A PISTON ROD OF A DRUG DELIVERY DEVICE, PISTON ROD COMPRISING THE BEARING COMPONENT, AND DRUG DELIVERY DEVICE

CROSS REFERENCE TO RELATED APPLICATIONS

The present application is a U.S. National Phase application pursuant to 35 U.S.C. § 371 of International Application No. PCT/EP2014/054525 filed Mar. 10, 2014, which claims priority to European Patent Application No. 13158513.5 filed Mar. 11, 2013. The entire disclosure contents of these applications are herewith incorporated by reference into the present application.

FIELD OF INVENTION

Bearing component for a piston rod of a drug delivery device, piston rod comprising the bearing component, and drug delivery device.

BACKGROUND

Drug delivery devices, in particular pen-type injection devices, comprise a bung, which serves to eject doses of a drug from a container like a drug cartridge and may be provided as part of a drug cartridge. The bung is driven by a piston rod, which may be provided with a mechanism for setting a dose and for advancing the piston rod to deliver the dose set. In some pen-type injection devices the piston rod comprises a lead screw, which rotates when it is advanced during dose dispense. As a rotation of the bung is preferably avoided, there will be a relative rotation of the piston rod with respect to the bung during dispense. In this case a direct contact between the piston rod and the bung may result in large frictional losses and in a rather strong driving force being required. This disadvantage may be avoided by a suitable bearing. Furthermore, it is desirable to have a contact between the bung and the piston rod over as large an area as possible, because a small contact area or a point contact is liable to cause a deformation of the bung during dispense, thus reducing dose accuracy. Therefore a bearing component is preferably arranged between the piston rod and the bung. The bearing component can be formed to engage a large surface area of the bung and to contact only a small surface area of the piston rod, in order to facilitate a relative rotation of a component of the piston rod, like a lead screw, with respect to the bearing component. The bearing component must be able to assemble to the lead screw at relatively low assembly forces and without risking component damage. The bearing component must not become detached from the lead screw following assembly or during the device life, as this can result in dose inaccuracies. The bearing features must be robust enough to withstand the rigors of automated assembly and bulk packing.

US 2007/0093761 A1 discloses a drive mechanism suitable for use in drug delivery devices comprising a piston rod and a generally cylindrical drive sleeve surrounding the piston rod. A thread of the piston rod is adapted to work within a helical groove extending along the internal surface of the drive sleeve. A further thread of the piston rod extends through a threaded opening of an insert. A longitudinal axial movement of the drive sleeve causes the piston rod to rotate according to the thread of the insert, thereby advancing the piston rod and thus driving a piston in the cartridge. A bearing is provided on the piston rod by a pressure foot, which abuts the cartridge piston.

SUMMARY

It is an object of the present invention to reduce frictional losses between a rotating piston rod and a bung for use in a drug delivery device.

This object is achieved with the bearing component according to claim 1, with the piston rod comprising the bearing component according to claim 8 and with the drug delivery device according to claim 12. Further embodiments derive from the dependent claims.

In one aspect the invention relates to a bearing component for a piston rod of a drug delivery device. The bearing component comprises a contact surface, a periphery, which surrounds a centre, and a coupling feature arranged inside the periphery for rotatably engaging a component of a piston rod perpendicular to the contact surface. The coupling feature includes a flexible feature extending from the periphery towards the centre, and the flexible feature is arranged to be deflected towards the periphery by a force exerted on the flexible feature in a direction towards the contact surface and deflected towards the centre by a force exerted on the flexible feature in the opposite direction. There may be only one flexible element, two flexible elements or more than two flexible elements.

In an embodiment of the bearing component, the flexible feature has sloping surfaces inclined with respect to the contact surface, the sloping surfaces approaching the contact surface towards the centre.

In a further embodiment the flexible feature is an integral part of the bearing component.

In a further embodiment the flexible feature is formed by at least one flexible arm, hook, prong, tooth or salient element.

In a further embodiment the centre comprises an opening, and the flexible feature limits the opening.

In a further embodiment the opening is enlarged when the flexible feature is deflected towards the periphery.

In a further embodiment the flexible feature is arranged such that the bearing component is symmetrical with respect to rotations by 180° around the centre.

In another aspect the invention relates to a piston rod comprising such a bearing component.

In an embodiment of the piston rod, the component of the piston rod that is rotatably engaged by the flexible feature is a lead screw.

In a further embodiment of the piston rod, the component of the piston rod that is rotatably engaged by the flexible feature comprises a coupler having an overhanging flange, and the bearing component engages the coupler with the flexible feature stopping the flange.

In a further embodiment of the piston rod, the component of the piston rod that is rotatably engaged by the flexible feature contacts the bearing component at least in a contact area near the periphery of the bearing component.

In another aspect the invention relates to a drug delivery device comprising such a bearing component, which may be mounted to a component of a piston rod. The drug delivery device may be an injection device, a pen-type device, and especially a pen-type injection device.

The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Igunit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE DRAWINGS

The following is a detailed description of embodiments of the bearing component and the piston rod comprising the bearing component in conjunction with the appended drawings.

DETAILED DESCRIPTION

Figure 1:
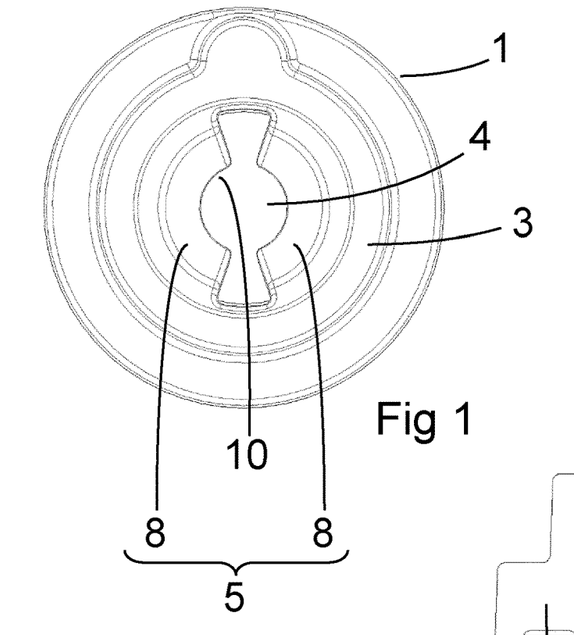
FIG. 1 is a top view of an embodiment of the bearing component.

FIG. 1 shows an embodiment of the bearing component in a top view. The bearing component 1 may have a generally circular shape, especially if the bearing component 1 is intended for a pen-type drug delivery device. At least one flexible feature 8 extends from the periphery 3 to the centre 4 and forms a coupling feature 5, which is used to fasten a further component of the piston rod. In the embodiment according to FIG. 1 the coupling feature 5 is formed by two flexible features 8, which are arranged in a rotationally symmetrical fashion with respect to rotations by 180° around the centre 4. A bearing 1 like this can be easily produced at lower cost. The two flexible features 8 each cover an angle of about 120°-160°, preferably about 150°. Although each flexible feature 8 is flexible enough to be resiliently movable during assembly, the inner edges of the flexible features 8 around opening 10 provide stability against twist. The stability increases with the angle of coverage. This stability helps preventing an inclination of the bearing component 1 with respect to the axis of the piston rod 7. Further, this ensures having an opening 10 large enough for a coupler 11 having an overhanging flange 12 to pass through. There may instead be only one flexible element 8 or more than two flexible elements 8. However, stability against twist decreases with the number of flexible elements. The coupling feature 5 may leave an opening 10 in the centre 4 of the bearing component 1. In this case the opening 10 is at least partially limited by the coupling feature 5.

Figure 2:
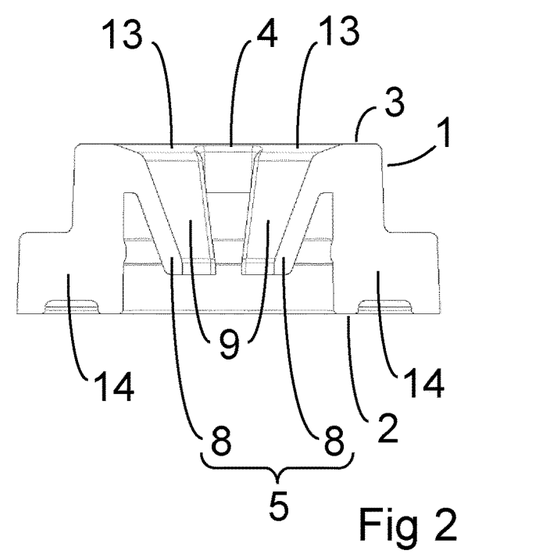
FIG. 2 is a cross section of the embodiment according to FIG. 1.

FIG. 2 is a cross section of the embodiment according to FIG. 1. The plane of the cross section is perpendicular to the top view shown in FIG. 1. The bearing component 1 preferably comprises a solid outer ring 14 forming the periphery 3 and providing mechanical stability of the bearing component 1. A contact surface 2 of the bearing component 1 is provided to push against a corresponding surface of a bung. The contact surface 2 may be on the front face of the outer ring 14. At the periphery 3 there is a contact area 13, which may partially cover the outer ring 14, the flexible features 8 or both the outer ring 14 and the flexible features 8.

The flexible features 8 of this embodiment have sloping surfaces 9, which are inclined with respect to the plane of the contact surface 2. The sloping surfaces 9 approach the contact surface 2 towards the centre 4, so that the coupling feature 5 grows narrower towards the plane of the contact surface 2. The flexible features 8 may be flexible arms, hooks, prongs, teeth or any other salient elements extending from the periphery 3 towards the centre 4. The flexible features 8 are preferably integral with the bearing component 1. The sloping surfaces 9 have the advantage that the assembly of the piston rod is facilitated, as will become apparent from the following description.

Figure 3:
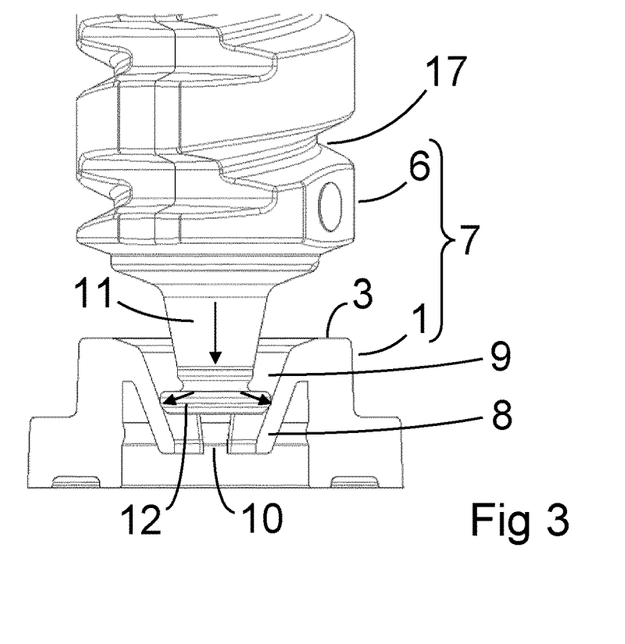
FIG. 3 shows a piston rod comprising the bearing component during assembly.

FIG. 3 shows a piston rod 7 comprising the bearing component 1 and a further component 6 in the state of being assembled. The bearing component 1 is shown in the cross section according to FIG. 2, whereas the further component 6 is shown in a perspective view. The further component 6 may be a lead screw having a screw thread 17, for example. The screw thread 17 may be employed in a drive mechanism to advance the piston rod 7. The further component 6 is moved relative to the bearing component 1 in the direction of the vertical arrow pointing downwards in FIG. 3. The end of the further component 6 facing the bearing component 1 comprises a coupler 11, which may resemble a spigot or pintle, for example. The coupler 11 is preferably provided with an overhanging flange 12. When the further component 6 is introduced in the opening 10 of the bearing component 1, the coupler 11 exerts a force on the sloping surfaces 9 of the flexible features 8, as indicated with the oblique arrows in FIG. 3. The flexible features 8 are thus pushed radially outward, and the opening 10 widens sufficiently to let the coupler 11 pass the edges of the flexible features 8.

Figure 4:
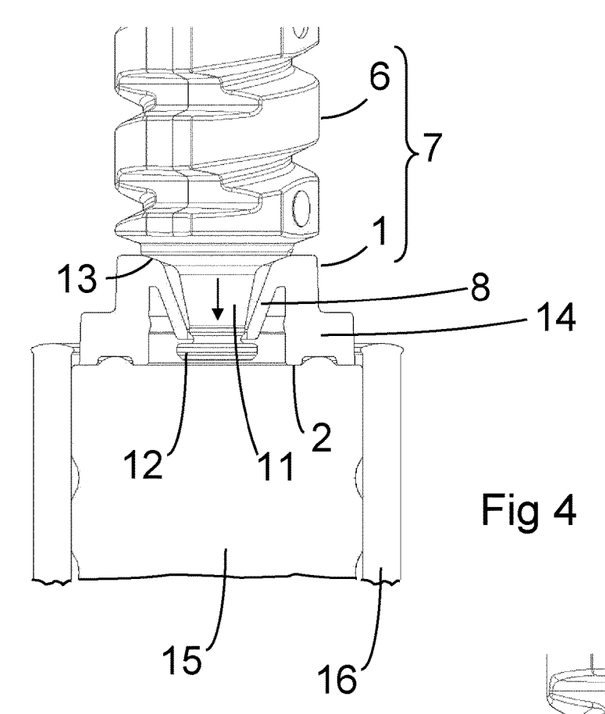
FIG. 4 shows the piston rod according to FIG. 3 after assembly.

FIG. 4 shows the piston rod 7 after the assembly. The flange 12 has been shifted beyond the edges of the flexible features 8, which have relaxed to their original position and axially lock the further component 6 by stopping the flange 12. The bearing component 1 can be brought into contact with a bung 15 of a drug cartridge 16. When the further component 6 is rotated, the coupler 11 can easily rotate within the bearing component 1, while the bearing component 1 and the bung 15 do not rotate with respect to one another. The contact area 13 and hence the friction between the components 1, 6 of the piston rod 7 is relatively small. The friction may be further reduced if the force advancing the piston rod 7 is also exerted by the flange 12 immediately on the bung 15, so that the pressure on the peripheral contact area 13 and hence the torque applied to the bearing component 1 by the further component 6 is reduced. Instead, the flange 12 may be kept at a distance from the bung 15. The contact surface 2 may be on the front face of the outer ring 14 facing the bung 15.

The flexible features 8 are preferably arranged within the outer ring 14 of the bearing component 1. The outer ring 14 protects the flexible features 8 from side loads that could arise if the device is subjected to impact or vibration or from direct loading on the component that might occur during an automated assembly or bulk transport situation. When the piston rod 7 is pushed towards the bung 15 during dispense, and the bearing component 1 is in compression, no load acts on the flexible features 8, so that the components 1, 6 stay securely coupled.

As shown in FIG. 4, the main component 6 of the piston rod 7 is pushed against contact area 13 on an outer ring 14 of the bearing component 1. The contact area 13 is small enough to keep the friction between the components 1 and 6 of the piston rod 7 at a low level and hence the torque applied to the bearing component 1 within tolerable limits. Reduced friction is particularly advantageous in case the piston rod is rotated during operation. It could be further reduced using low friction polymers. The contact area 13 is inclined towards the axis of the piston rod and adapted to the shape of the corresponding contact surface of the main component 6 e.g., a shape of a circumferential surface of a truncated cone. The contact area 13 prevents an inclination of the bearing component 1 with respect to the axis of the piston rod 7, when advanced, e.g. during assembly and/or during dispense operation. In addition, an inclined contact surface area 13 helps guiding the bearing component 1 to be and/or remain in line with the axis of the piston rod. This is particularly beneficial in case of a rotating piston rod 7. Flange 12 is kept at a distance from the bung 15 and has a contact surface 2 on the front face of the outer ring 14 facing the bung 15. A force driving the piston rod 7 is thus transferred to the bung 15 via the bearing component 1, in particular contact surface 2. Thus piston rod 7 is free to rotate while its push force is transferred to the bung 15 via the contact surface 2 of bearing 1. This embodiment may therefore be preferred if the piston rod is rotated during operation.

Figure 5:
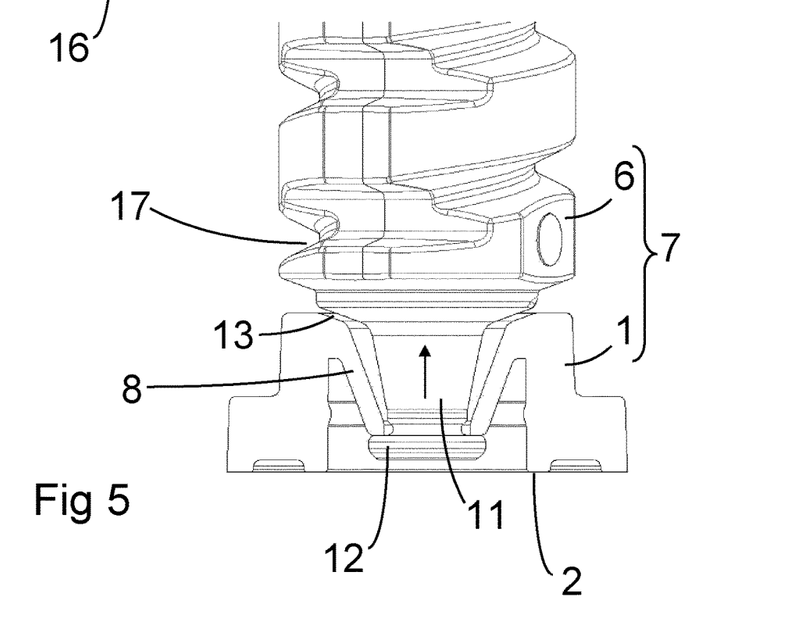
FIG. 5 shows the piston rod according to FIG. 4 subjected to a disassembly force.

FIG. 5 shows how a disassembly of the piston rod 7 is prevented. If an axial force is applied to the further component 6 relative to the bearing component 1 in the direction indicated with the vertical arrow in FIG. 5, the components 1, 6 are slightly separated. FIG. 5 shows the contact area 13 on the bearing component 1 no longer covered by the further component 6, owing to the action of the separating force, and the distance between the flange 12 and the plane of the contact area 2 being increased. In this state the flexible features 8 engage the flange 12 of the coupler 11. If the flexible features 8 have a sloping shape as in the described embodiment, this engagement with the flange 12 forces the flexible features 8 to deform inwards and dig into the coupler 11. This prevents a disassembly of the components 1, 6 of the piston rod 7, unless unusually great forces are applied.

The invention claimed is:

1. A piston rod for pushing a bung of a drug cartridge, the piston rod comprising:
    a lead screw comprising a first coupler comprising a central portion extending along a longitudinal axis of the piston rod and an overhanging flange extending radially outward from the central portion and extending continuously around the central portion; and
    a bearing component, wherein the bearing component comprises
        a distal contact surface configured to push against a corresponding surface of the bung for advancing the bung during a dispense operation,
        a solid outer ring forming a periphery surrounding a center of the bearing component, the solid outer ring providing mechanical stability for the bearing component, and
        a second coupler arranged inside the periphery for rotatably engaging the first coupler of the lead screw such that the first coupler is rotatable within the bearing component about the longitudinal axis of the piston rod,
    wherein the lead screw extends perpendicularly to the distal contact surface,
    wherein the second coupler of the bearing component includes two flexible arms extending from the periphery towards the center,
    wherein the two flexible arms are arranged to be deflected towards the periphery by a force exerted by the overhanging flange on the two flexible arms in a distal direction towards the distal contact surface and deflected towards the center by a force exerted by the overhanging flange on the two flexible arms in a proximal direction opposite the distal direction,
    wherein the lead screw contacts the bearing component at least in a contact area of the bearing component, and
    wherein the contact area partially covers the outer ring, wherein the contact area is inclined towards the longitudinal axis of the piston rod and the lead screw comprises a corresponding contact surface that is inclined relative to the longitudinal axis of the piston rod such that the overhanging flange is kept at a distance from a plane of the distal contact surface, wherein the contact area forms a friction surface between the bearing component and the lead screw when the lead screw is rotated and forced in the distal direction, and wherein the two flexible arms extend directly from the contact area, wherein the piston rod is adapted such that a force driving the lead screw is transferred to the bung via the distal contact surface of the bearing component during the dispense operation, wherein the lead screw is free to rotate relative to the bearing component and the bung while the driving force is transferred to the bung via the distal contact surface of the bearing component, and
    wherein each of the two flexible arms covers an angle in a rotational direction about the longitudinal axis, the angle being between 120 to 160 degrees.

2. The piston rod according to claim 1, wherein the two flexible arms have sloping surfaces inclined with respect to the distal contact surface, the sloping surfaces approaching the distal contact surface towards the center.

3. The piston rod according to claim 1, wherein the two flexible arms are integral parts of the bearing component.

4. The piston rod according to claim 1, wherein the two flexible arms define an opening.

5. The piston rod according to claim 4, wherein the opening defined by the two flexible arms is enlarged when the flexible arms are deflected towards the periphery.

6. The piston rod according to claim 1, wherein the flexible arms are arranged such that the bearing component is symmetrical with respect to rotations by 180 degrees around the center.

7. The piston rod according to claim 1, wherein the bearing component engages the second coupler with the two flexible arms stopping the overhanging flange.

8. The piston rod according to claim 1, wherein the contact area is adapted to a shape of a corresponding contact surface of the lead screw.

9. The piston rod according to claim 1, wherein the lead screw is configured to rotate when it is advanced during dose dispense.

10. The piston rod of claim 1, wherein the contact area faces in a first longitudinal direction opposite a second longitudinal direction in which the distal contact surface faces.

11. The piston rod of claim 10, wherein the two flexible arms extend longitudinally in the second longitudinal direction from the contact area toward the distal contact surface.

12. The piston rod according to claim 1, wherein the distal contact surface is configured to directly push against the corresponding surface of the bung,
    wherein a through-hole extends along the longitudinal axis of the piston rod along an entire length of the bearing component, the periphery surrounding the through-hole, the center of the bearing component being located within the through-hole, and the two flexible arms extending from the periphery into the through-hole towards the center, and
    wherein the piston rod is in an assembled state in which
        the overhanging flange is inserted into the through-hole and axially locked by the two flexible arms such that movement of the overhanging flange in the proximal direction is limited, and
        the corresponding contact surface of the lead screw has a shape of a circumferential surface of a truncated cone.

13. A drug delivery device comprising:
a housing; and
a piston rod for pushing a bung of a drug cartridge, the piston rod being at least partially disposed in the housing and comprising:
    a lead screw comprising a first coupler comprising a central portion extending along a longitudinal axis of the piston rod and an overhanging flange extending radially outward from the central portion and extending continuously around the central portion; and
    a bearing component, wherein the bearing component comprises
        a distal contact surface configured to push against a corresponding surface of the bung for advancing the bung during a dispense operations, a solid outer ring forming a periphery surrounding a center of the bearing component, the solid outer ring providing mechanical stability for the bearing component, and a second coupler arranged inside the periphery for rotatably engaging the first coupler of the lead screw such that the first coupler is rotatable within the bearing component about the longitudinal axis of the piston rod, wherein the lead screw extends perpendicularly to the distal contact surface, wherein the second coupler of the bearing component includes two flexible arms extending from the periphery towards the center, wherein the two flexible arms arranged to be deflected towards the periphery by a force exerted by the overhanging flange on the two flexible arms in a distal direction towards the distal contact surface and deflected towards the center by a force exerted by the overhanging flange on the two flexible arms in a proximal direction opposite the distal direction, wherein the lead screw contacts the bearing component at least in a contact area of the bearing component, and wherein the contact area partially covers the outer ring, wherein the contact area is inclined towards the longitudinal axis of the piston rod and the lead screw comprises a corresponding contact surface that is inclined relative to the longitudinal axis of the piston rod such that the overhanging flange is kept at a distance from a plane of the distal contact surface, wherein the contact area forms a friction surface between the bearing component and the lead screw when the lead screw is rotated and forced in the distal direction, and wherein the two flexible arms extend directly from the contact area, wherein the piston rod is adapted such that a force driving the lead screw is transferred to the bung via the distal contact surface of the bearing component during the dispense operation, wherein the lead screw is free to rotate relative to the bearing component and the bung while the driving force is transferred to the bung via the distal contact surface of the bearing component, and wherein each of the two flexible arms covers an angle in a rotational direction about the longitudinal axis, the angle being between 120 to 160 degrees.

14. The drug delivery device of claim 13, wherein the bearing component is mounted to the lead screw.

15. The drug delivery device of claim 13, the drug delivery device being an injection device.

16. The drug delivery device of claim 13, the drug delivery device being a pen-type device.

17. The drug delivery device according to claim 13, wherein the distal contact surface is configured to directly push against the corresponding surface of the bung, wherein a through-hole extends along the longitudinal axis of the piston rod along an entire length of the bearing component, the periphery surrounding the through-hole, the center of the bearing component being located within the through-hole, and the two flexible arms extending from the periphery into the through-hole towards the center, and wherein the piston rod is in an assembled state in which the overhanging flange is inserted into the through-hole and axially locked by the two flexible arms such that movement of the overhanging flange in the proximal direction is limited, and the corresponding contact surface of the lead screw has a shape of a circumferential surface of a truncated cone.

18. A piston rod for pushing a bung of a drug cartridge, the piston rod comprising:

a lead screw comprising a first coupler comprising a central portion extending along a longitudinal axis of the piston rod and an overhanging flange extending radially outward from the central portion and extending continuously around the central portion; and a bearing component, wherein the bearing component comprises a distal contact surface configured to push against a corresponding surface of the bung for advancing the bung during a dispense operation, a solid outer ring forming a periphery surrounding a center of the bearing component, the solid outer ring providing mechanical stability for the bearing component, and a second coupler arranged inside the periphery for rotatably engaging the first coupler of the lead screw such that the first coupler is rotatable within the bearing component about the longitudinal axis of the piston rod, wherein the lead screw extends perpendicularly to the distal contact surface, wherein the second coupler of the bearing component includes two flexible arms extending from the periphery towards the center, wherein the two flexible arms are arranged to be deflected towards the periphery by a force exerted by the overhanging flange on the two flexible arms in a distal direction towards the distal contact surface and deflected towards the center by a force exerted by the overhanging flange on the two flexible arms in a proximal direction opposite the distal direction, wherein the lead screw contacts the bearing component at least in a contact area of the bearing component, and wherein the contact area partially covers both the outer ring and the two flexible arms, wherein the contact area covers a radially outer end of each of the two flexible arms, the radially outer ends adjoined to the periphery, wherein the contact area is inclined towards the longitudinal axis of the piston rod and the lead screw comprises a corresponding contact surface that is inclined relative to the longitudinal axis of the piston rod such that the overhanging flange is kept at a distance from a plane of the distal contact surface, wherein the contact area forms a friction surface between the bearing component and the lead screw when the lead screw is rotated and forced in the distal direction, and wherein the two flexible arms extend directly from the contact area and along the contact area toward the center, wherein the piston rod is adapted such that a force driving the lead screw is transferred to the bung via the distal contact surface of the bearing component during the dispense operation, wherein the lead screw is free to rotate relative to the bearing component and the bung while the driving force is transferred to the bung via the distal contact surface of the bearing component, and wherein each of the two flexible arms covers an angle in a rotational direction about the longitudinal axis, the angle being between 120 to 160 degrees.

19. The piston rod according to claim 18, wherein the distal contact surface is configured to directly push against the corresponding surface of the bung, wherein a through-hole extends along the longitudinal axis of the piston rod along an entire length of the bearing component, the periphery surrounding the through-hole, the center of the bearing component being located within the through-hole, and the two flexible arms extending from the periphery into the through-hole towards the center, and wherein the piston rod is in an assembled state in which the overhanging flange is inserted into the through-hole and axially locked by the two flexible arms such that movement of the overhanging flange in the proximal direction is limited, and the corresponding contact surface of the lead screw has a shape of a circumferential surface of a truncated cone.

20. A piston rod for pushing a bung of a drug cartridge, wherein the piston rod comprises:

a lead screw comprising a first coupler comprising a central portion extending along a longitudinal axis of the piston rod and an overhanging flange extending radially outward from the central portion and extending continuously around the central portion; and a bearing component, wherein the bearing component comprises a distal contact surface configured to push against a corresponding surface of the bung for advancing the bung during a dispense operation, a solid outer ring forming a periphery surrounding a center of the bearing component, the solid outer ring providing mechanical stability for the bearing component, and a second coupler arranged inside the periphery for rotatably engaging the first coupler of the lead screw such that the first coupler is rotatable within the bearing component about the longitudinal axis of the piston rod, wherein the lead screw extends perpendicularly to the distal contact surface, wherein the second coupler includes two flexible arms extending from the periphery towards the center, wherein the two flexible arms are arranged to be deflected towards the periphery by a force exerted by the overhanging flange on the two flexible arms in a distal direction towards the distal contact surface and deflected towards the center by a force exerted by the overhanging flange on the two flexible arms in a proximal direction opposite the distal direction, wherein the lead screw contacts the bearing component at least in a contact area of the bearing component, and wherein the contact area partially covers the two flexible arms, wherein the contact area covers a radially outer end of each of the two flexible arms, the radially outer ends adjoined to the periphery, wherein the contact area is inclined towards the longitudinal axis of the piston rod and the lead screw comprises a corresponding contact surface that is inclined relative to the longitudinal axis of the piston rod such that the overhanging flange is kept at a distance from a plane of the distal contact surface, wherein the contact area forms a friction surface between the bearing component and the lead screw when the lead screw is rotated and forced in the distal direction, wherein the piston rod is adapted such that a force driving the lead screw is transferred to the bung via the distal contact surface of the bearing component during the dispense operation, wherein the lead screw is free to rotate relative to the bearing component and the bung while the driving force is transferred to the bung via the distal contact surface of the bearing component, and wherein each of the two flexible arms covers an angle in a rotational direction about the longitudinal axis, the angle being between 120 to 160 degrees.

21. The piston rod according to claim 20, wherein the distal contact surface is configured to directly push against the corresponding surface of the bung, wherein a through-hole extends along the longitudinal axis of the piston rod along an entire length of the bearing component, the periphery surrounding the through-hole, the center of the bearing component being located within the through-hole, and the two flexible arms extending from the periphery into the through-hole towards the center, wherein the piston rod is in an assembled state in which the overhanging flange is inserted into the through-hole and axially locked by the two flexible arms such that movement of the overhanging flange in the proximal direction is limited, and the corresponding contact surface of the lead screw has a shape of a circumferential surface of a truncated cone.

* * * * *